(12) United States Patent
Dunn et al.

(10) Patent No.: US 11,744,491 B2
(45) Date of Patent: Sep. 5, 2023

(54) NONINVASIVE METHOD AND APPARATUS FOR PERIPHERAL ASSESSMENT OF VASCULAR HEALTH

(71) Applicant: The Regents of the University of California, Oakland, CA (US)

(72) Inventors: Cody Dunn, Irvine, CA (US); Christian Crouzet, Irvine, CA (US); Bernard Choi, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 513 days.

(21) Appl. No.: 15/931,350

(22) Filed: May 13, 2020

(65) Prior Publication Data

US 2020/0359948 A1    Nov. 19, 2020

Related U.S. Application Data

(60) Provisional application No. 62/847,673, filed on May 14, 2019.

(51) Int. Cl.
| | |
|---|---|
| *A61B 5/1455* | (2006.01) |
| *A61B 5/00* | (2006.01) |
| *A61B 5/01* | (2006.01) |
| *A61B 5/02* | (2006.01) |

(52) U.S. Cl.
CPC ........ *A61B 5/14551* (2013.01); *A61B 5/0004* (2013.01); *A61B 5/01* (2013.01); *A61B 5/02007* (2013.01); *A61B 5/6826* (2013.01); *A61B 2503/045* (2013.01)

(58) Field of Classification Search
CPC ............. A61B 5/1455; A61B 5/14551; A61B 5/02007; A61B 5/6826; A61B 2503/045
See application file for complete search history.

(56) References Cited

U.S. PATENT DOCUMENTS

| | | | | |
|---|---|---|---|---|
| 5,490,523 A | * | 2/1996 | Isaacson | A61B 5/6826 |
| | | | | 600/323 |
| 7,299,079 B2 | * | 11/2007 | Rebec | A61B 5/1495 |
| | | | | 600/316 |
| 2016/0058300 A1 | * | 3/2016 | Yoon | A61B 5/681 |
| | | | | 600/480 |

* cited by examiner

*Primary Examiner* — Eric F Winakur
(74) *Attorney, Agent, or Firm* — Gavrilovich, Dodd & Lindsey LLP

(57) ABSTRACT

The technology relates to medical devices for monitoring and assessing vascular health. In one embodiment, the technology is an apparatus that attaches to a subject's finger comprising a heating and cooling component, a coherent source, a temperature sensor, an image detector, and/or a component for data control and management. In another embodiment, there is a component that alters local blood flow in the subject, and laser speckle contrast and photoplethysmography (PPG) signals from the altered blood flow in the subject are compared to monitor the vascular health of the subject.

20 Claims, 18 Drawing Sheets

Figure 1.
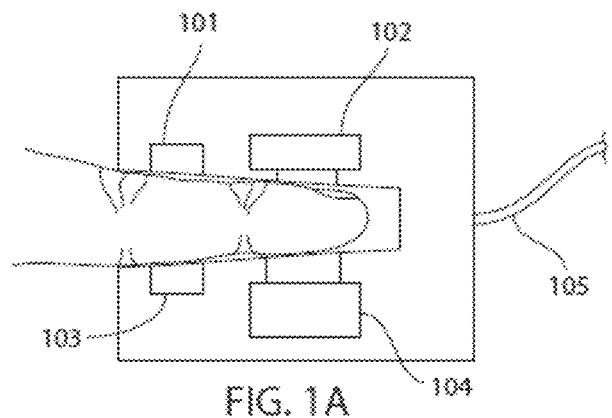
FIG. 1A
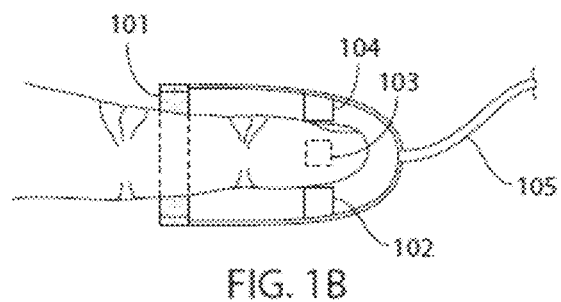
FIG. 1B
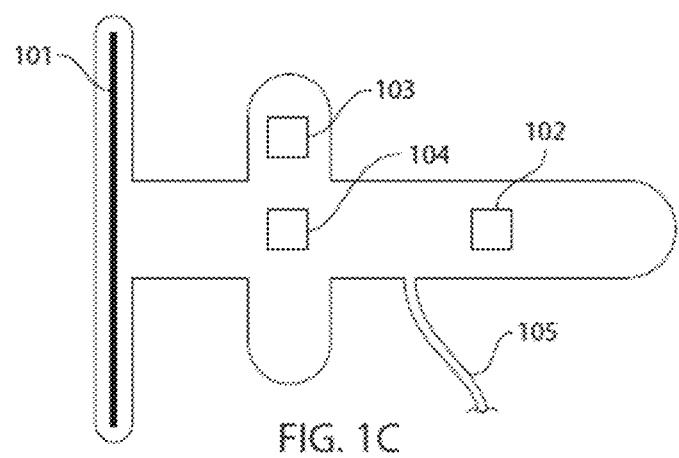
FIG. 1C

At steady state:

Subject 1

Subject 2

Subject 3

Figure 7.
Figure 7(a).
Subject 1:
PPG
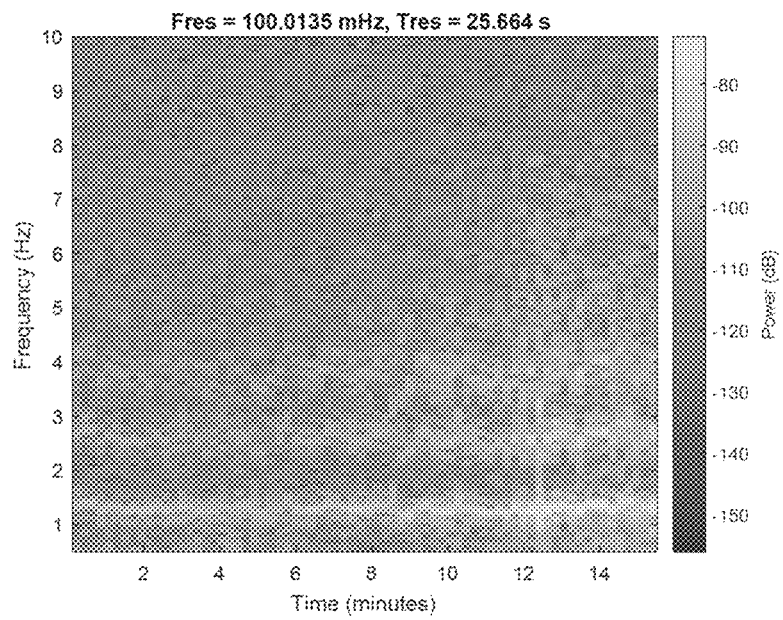
SPG
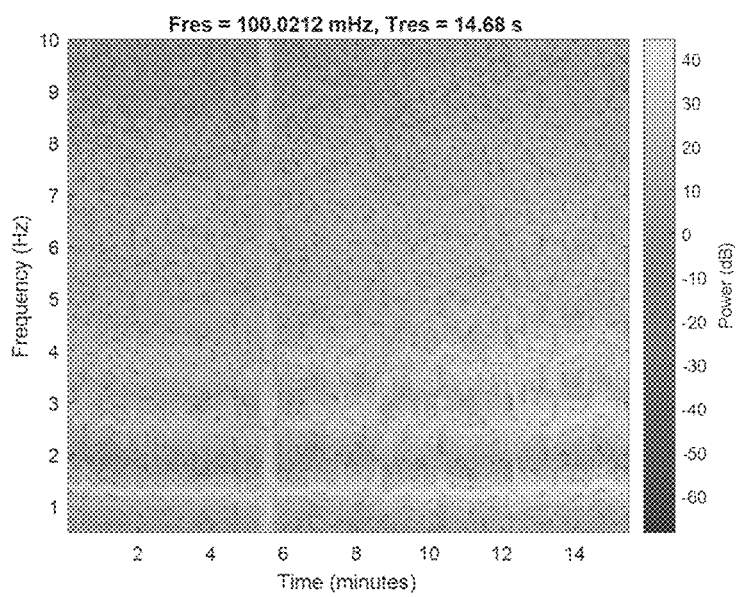

Subject 2:
PPG

SPG

Subject 3:
PPG

SPG

NONINVASIVE METHOD AND APPARATUS FOR PERIPHERAL ASSESSMENT OF VASCULAR HEALTH

CROSS-REFERENCE TO RELATED APPLICATIONS

The present application claims the benefit of priority under 35 U.S.C. § 119(e) of provisional application Ser. No. 62/847,673, filed May 14, 2019, the contents of which are hereby incorporated by reference.

FIELD OF THE INVENTION

The present disclosure relates to the medical field, and more specifically, medical devices for monitoring and assessing health.

BACKGROUND OF THE INVENTION

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

A common method in the art for determining endothelial function is invasive and requires administration of the drugs adenosine and acetylcholine. Accepted noninvasive solutions require the use of a cuff to occlude blood flow, which is time-consuming and uncomfortable for the patient. Noninvasive blood pressure monitoring also generally requires an uncomfortable cuff and is non-continuous. For both endothelial function and blood pressure, current cuffless systems are not widely used due to unacceptable levels of accuracy. A common standard for measuring arterial stiffness noninvasively involves multiple expensive tonometry sensors at different locations on the body. Current single-location methods often lacks accuracy. For these reasons, often endothelial function and arterial stiffness are not routinely tested even though they are accurate predictors of cardiovascular risk. Thus, there is a need in the art for novel and more effective devices and methods of use thereof for measuring and managing vascular health.

SUMMARY OF THE INVENTION

Various embodiments include a device for managing and/or monitoring vascular health, comprising an apparatus comprising a heating component, a cooling component, a coherent source, a temperature sensor, an image detector, and/or a component for data control and management, wherein the apparatus can be attached to a subject's finger. In another embodiment, the component for data control and management comprises wiring to a power source, control circuitry, and/or image processing. In another embodiment, the component for data control and management is wireless. In another embodiment, the apparatus is a clip to the finger. In another embodiment, the apparatus is a flexible design. In another embodiment, the device is used in conjunction with multiple wavelengths, multiple exposure times, and/or multiple detectors. In another embodiment, the device uses a wavelength between visible to near infrared. In another embodiment, the device uses multiple wavelengths to aid in the calculation of oxygen saturation. In another embodiment, the device uses multiple exposure times that range from 0.05 ms to 80 ms. In another embodiment, the device uses multiple exposure times that range from 0.02 ms to 100 ms. In another embodiment, the device uses more than one exposure time to aid in establishing baseline flow measurements that are quantitative. In another embodiment, the device comprises multiple detectors. In another embodiment, the device comprises a first detector to measure SPG and a second detector to measure PPG. In another embodiment, the SPG detector is a camera sensor, photodetector and/or photodiode array. In another embodiment, the PPG detector is a camera sensor and/or photodetector.

Other embodiments include a device for monitoring vascular health in a subject, comprising a heating/cooling component that alters local blood flow in the subject, and an apparatus that compares laser speckle contrast and photoplethysmography (PPG) signals from the altered blood flow in the subject. In another embodiment, the vascular health is monitored using a coherent source and a detector that compares the laser speckle contrast and PPG. In another embodiment, wherein the heating/cooling component is attached as a clip to the subject's finger. In another embodiment, the device is worn around the wrist of the subject.

Other embodiments include a method of diagnosing susceptibility to a disease and/or condition in a subject, comprising providing a device for monitoring vascular health in a subject, comprising a heating/cooling component that alters local blood flow in the subject and an apparatus that compares laser speckle contrast and photoplethysmography (PPG) signals from the altered blood flow in the subject, and diagnosing susceptibility to the disease based on the presence of one or more biomarkers. In another embodiment, the disease is related to vascular health. In another embodiment, the subject is a neonate and/or premature infant.

Other features and advantages of the invention will become apparent from the following detailed description, taken in conjunction with the accompanying drawings, which illustrate, by way of example, various embodiments of the invention.

DESCRIPTION OF THE FIGURES

FIG. 1 depicts, in accordance with embodiments herein, various examples of a device for monitoring and assessing health, and components thereof. Specifically, in accordance with various embodiments herein, the figure depicts a device with a heating/cooling component 101, coherent source 102, temperature sensor 103, image detector 104, and wiring 105 (to power source and control circuitry and image processing). In another embodiment, the wiring 105 is actually wireless and without a physical wire, where data analysis and control may be performed wirelessly. FIG. 1(a) depicts an example of the device that is a rigid encasing model. FIG. 1(b) depicts an example of the device that is a model of relatively more flexible circuitry and design. FIG. 1(c) depicts the model of relatively more flexible circuitry and design as illustrated on a user's finger.

FIG. 7 depicts, in accordance with embodiments herein, in vivo SPG/PPG testing on healthy humans with dynamic temperature change, with frozen corn placed on subject and then slowly increased temperature to 40° C. with a heating pad until corn entirely thawed. In vivo SPG/PPG testing on healthy humans with dynamic temperature change was conducted. Frozen corn was placed on the subject, and then slowly increased temperature to 40° C. with a heating pad until the corn was entirely thawed. Some features of note: Spectrogram has increased frequency content at higher temperatures (significantly more power for the SPG signal); increasing DC values for SPG and PPG signals with temperature increase.

DETAILED DESCRIPTION

Figure 2:
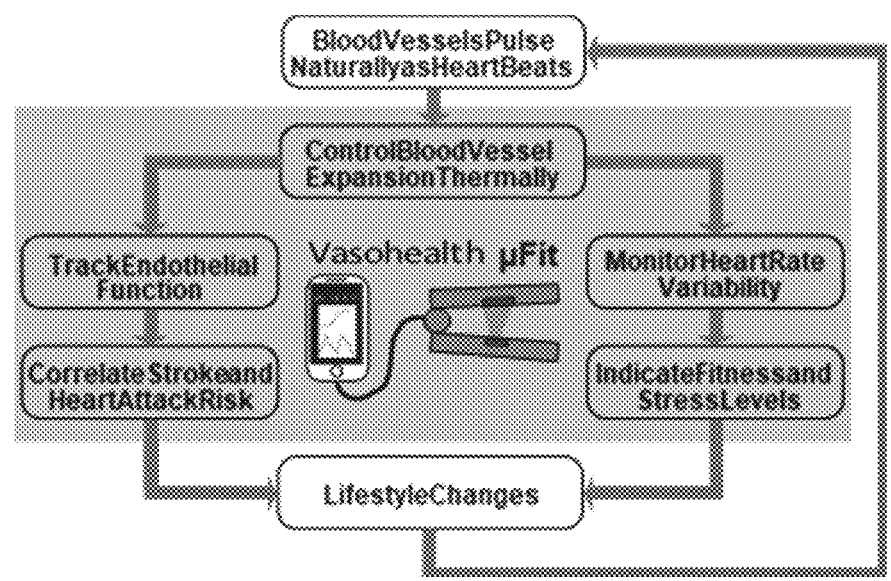
FIG. 2 depicts, in accordance with embodiments herein, a flow chart demonstrating examples of various health conditions and metrics that may be managed and monitored by devices further described herein.
Figure 3:
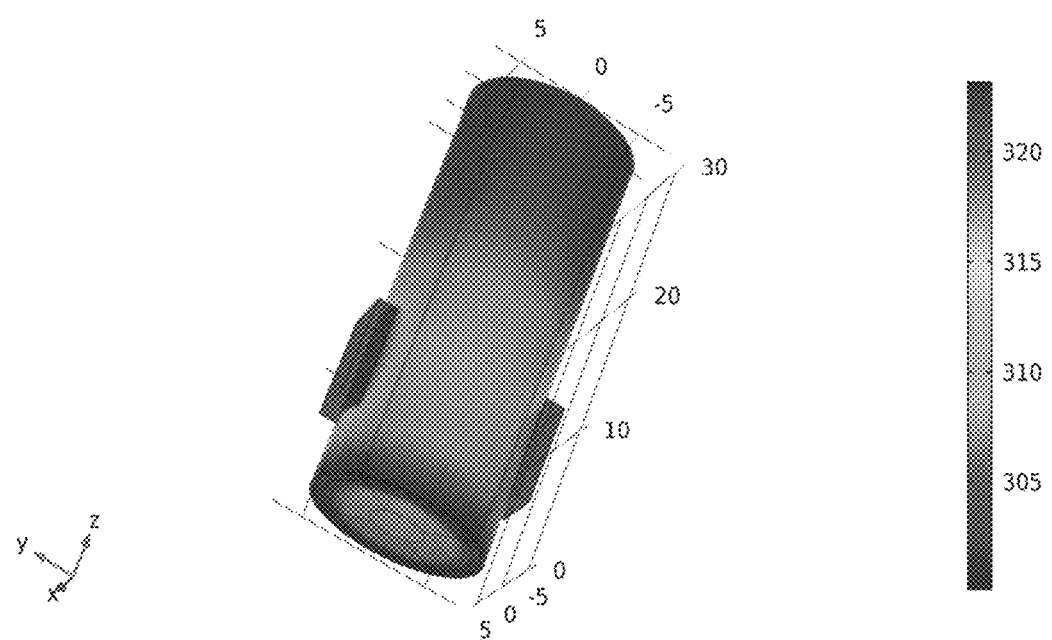
FIG. 3 depicts, in accordance with embodiments herein, results demonstrating five layers with different initial temperature. For heat source, bottom surface T=42° C. Other surfaces, q=0 (heat insulation condition). Boundary Condition I; III: Constant temperature (34° C. and 27° C.); I, IV, and the symmetric surface of IV: heat convection with air (Tair=24° C.); II and the symmetric surface of II: q=0 (heat insulation).
Figure 3:
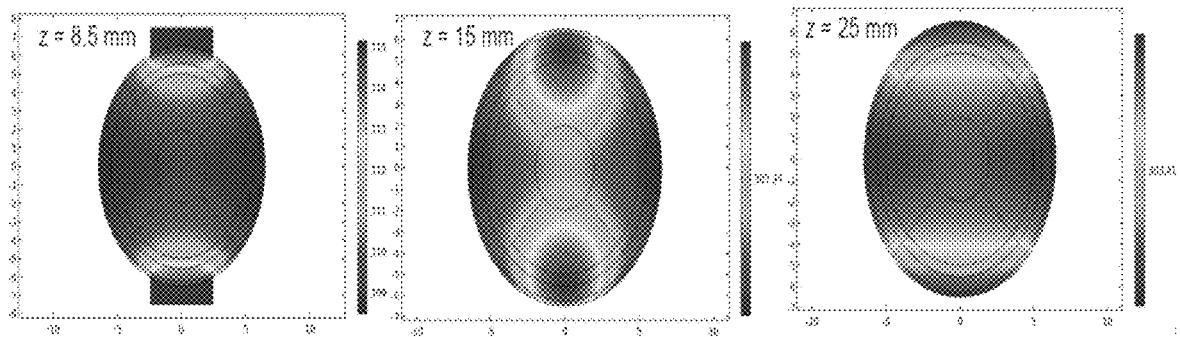
Figure 4:
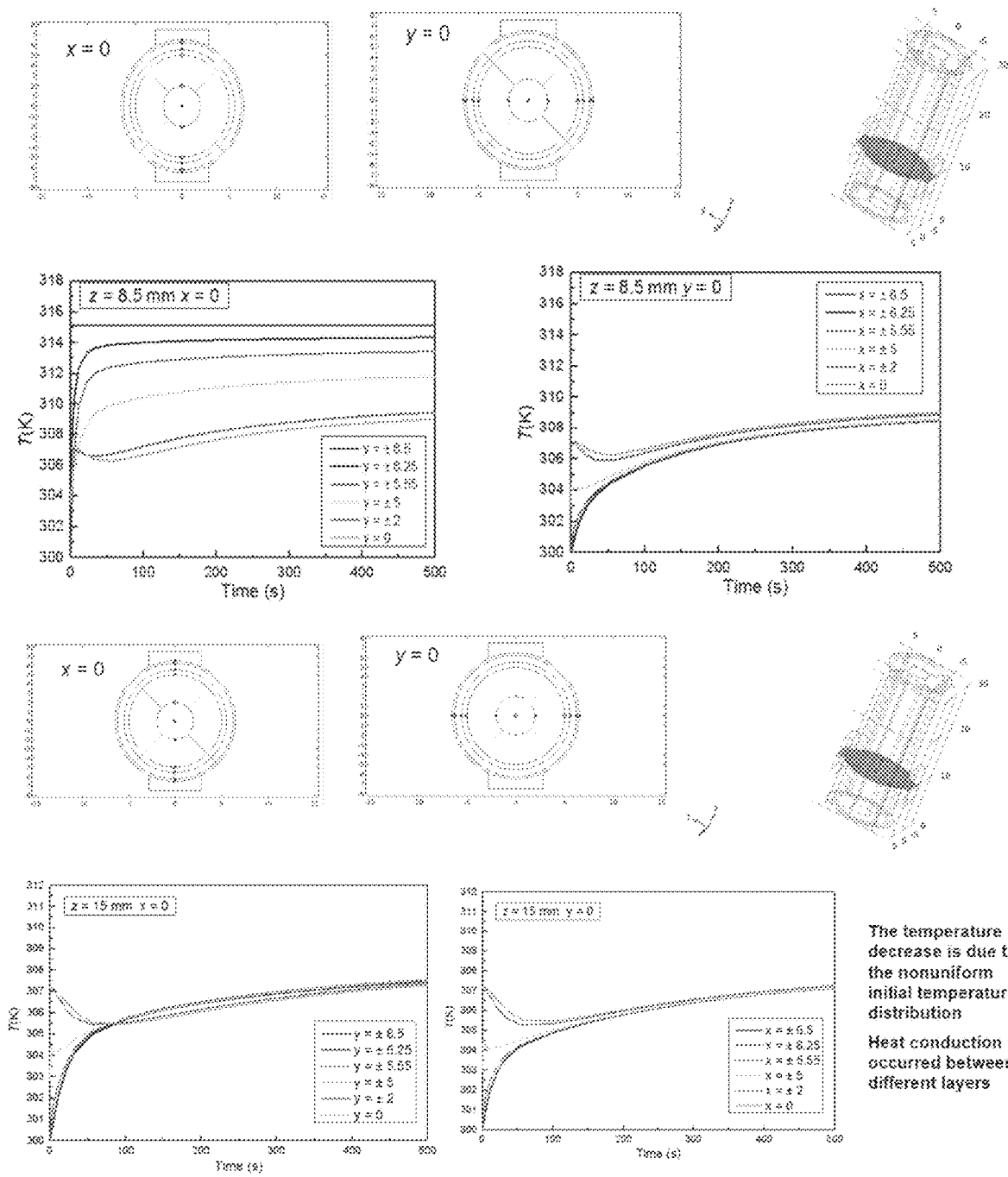
FIG. 4 depicts, in accordance with embodiments herein, results demonstrating heat conductions between different layers, in support of the efficacy of various embodiments herein for devices that manage and monitor various health conditions and metrics.
Figure 5:
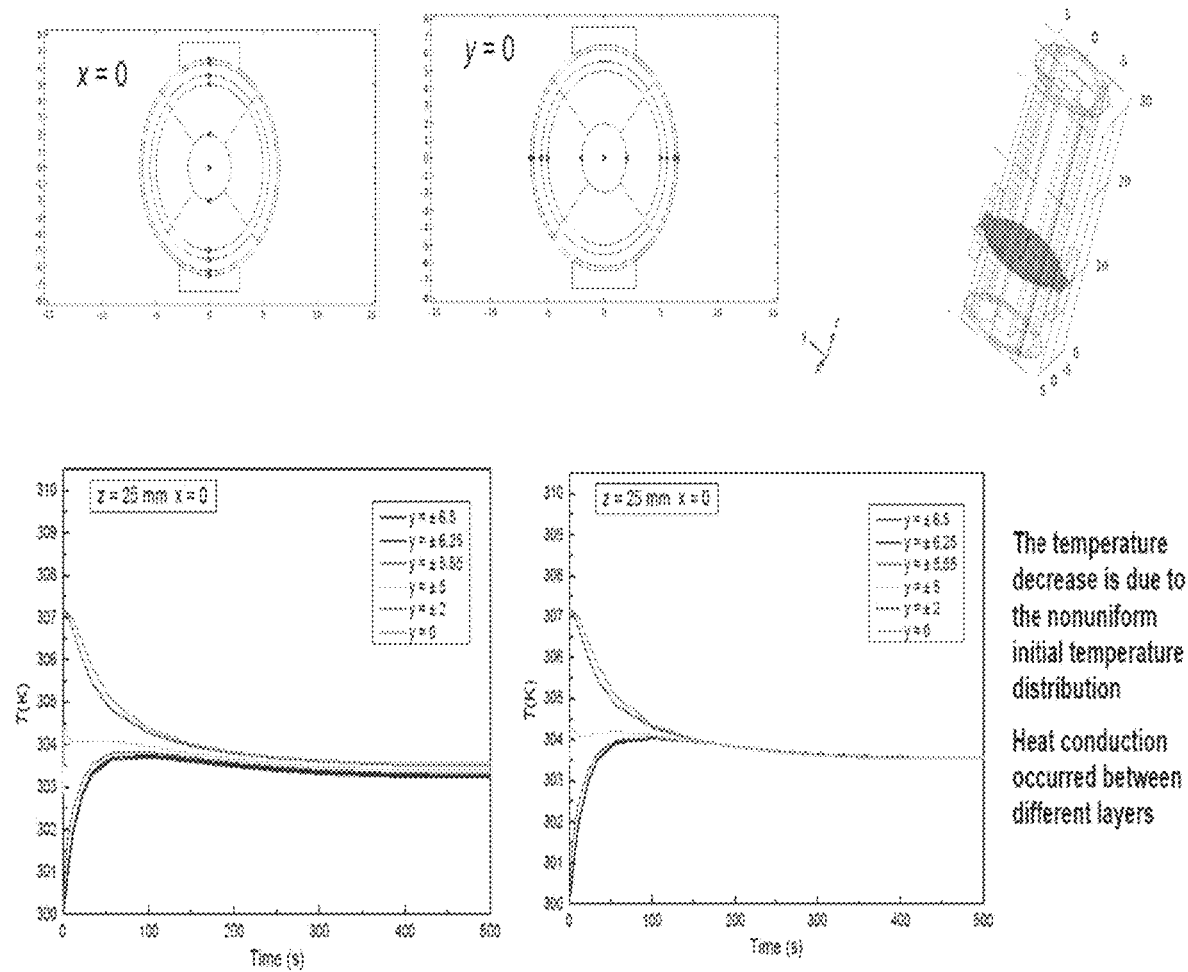
FIG. 5 depicts, in accordance with embodiments herein, results demonstrating heat conductions between different layers, in support of the efficacy of various embodiments herein for devices that manage and monitor various health conditions and metrics.
Figures 6, 6A:
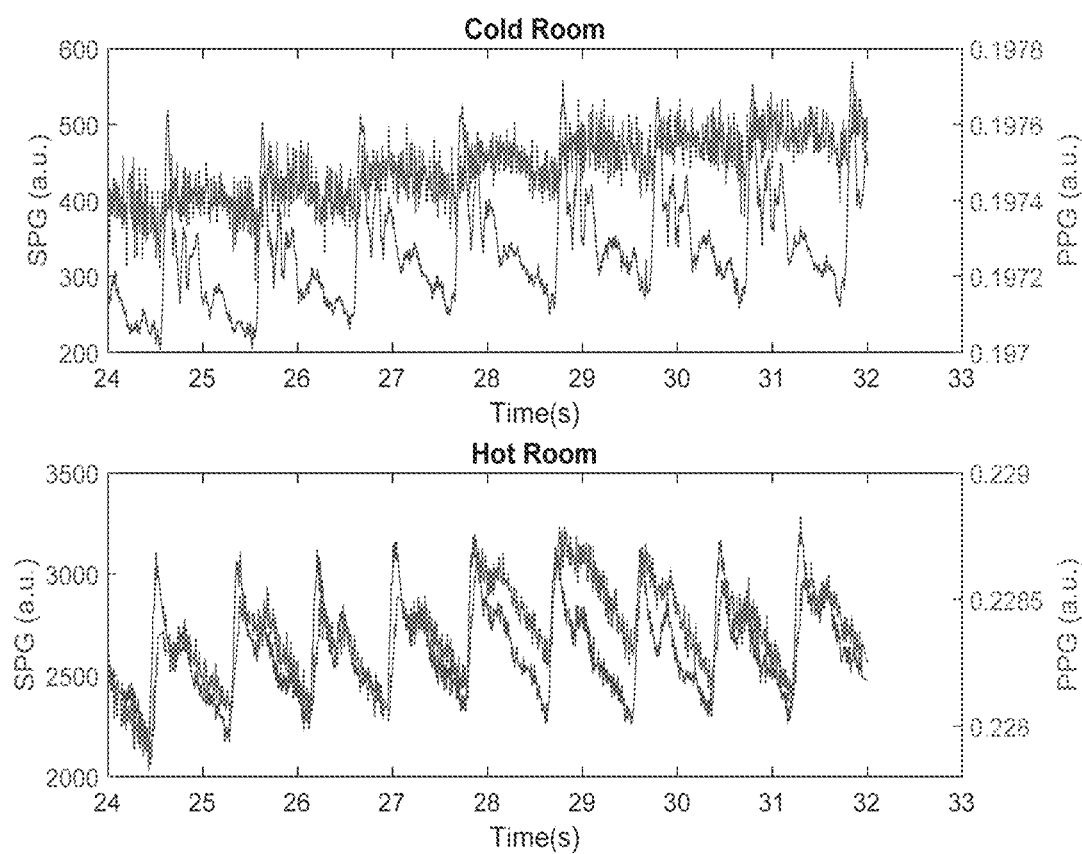
FIG. 6 depicts, in accordance with embodiments herein, in vivo SPG/PPG testing on healthy humans at different temperatures while seated (Cold Room≈65° F.; Hot Room≈75° F.). Some features of note: Less noisy PPG at higher temperatures; and less chaotic tail, or "bumps," in SPG signal at higher temperature.
FIG. 6(a) depicts subject 1.
Figure 6B:
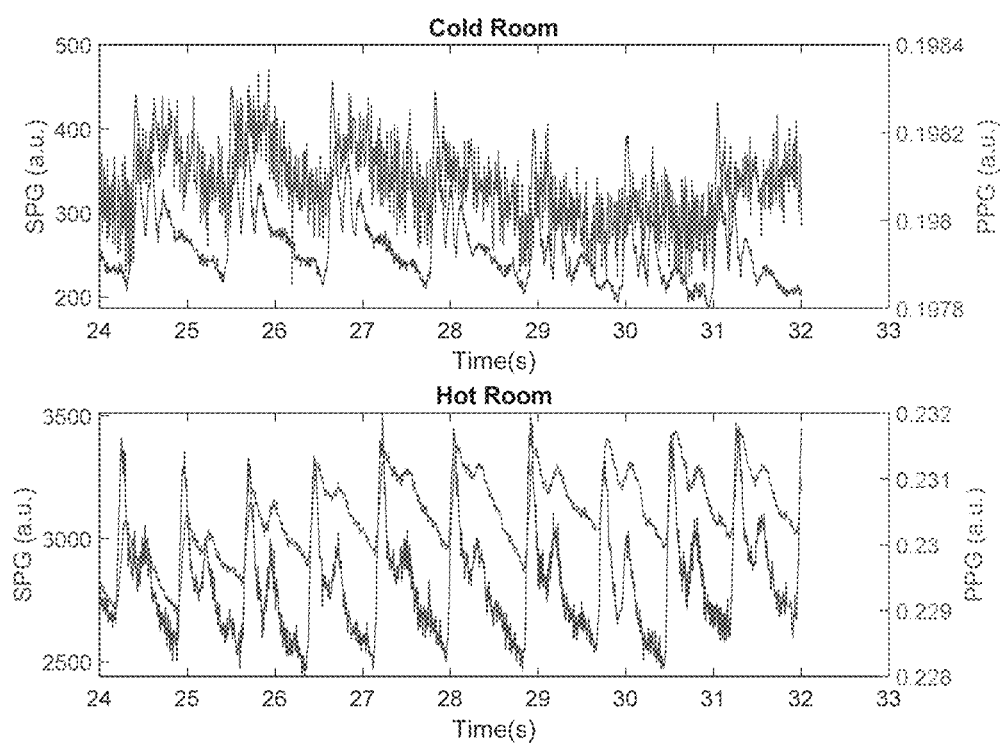
FIG. 6(b) depicts subject 2.
Figure 6C:
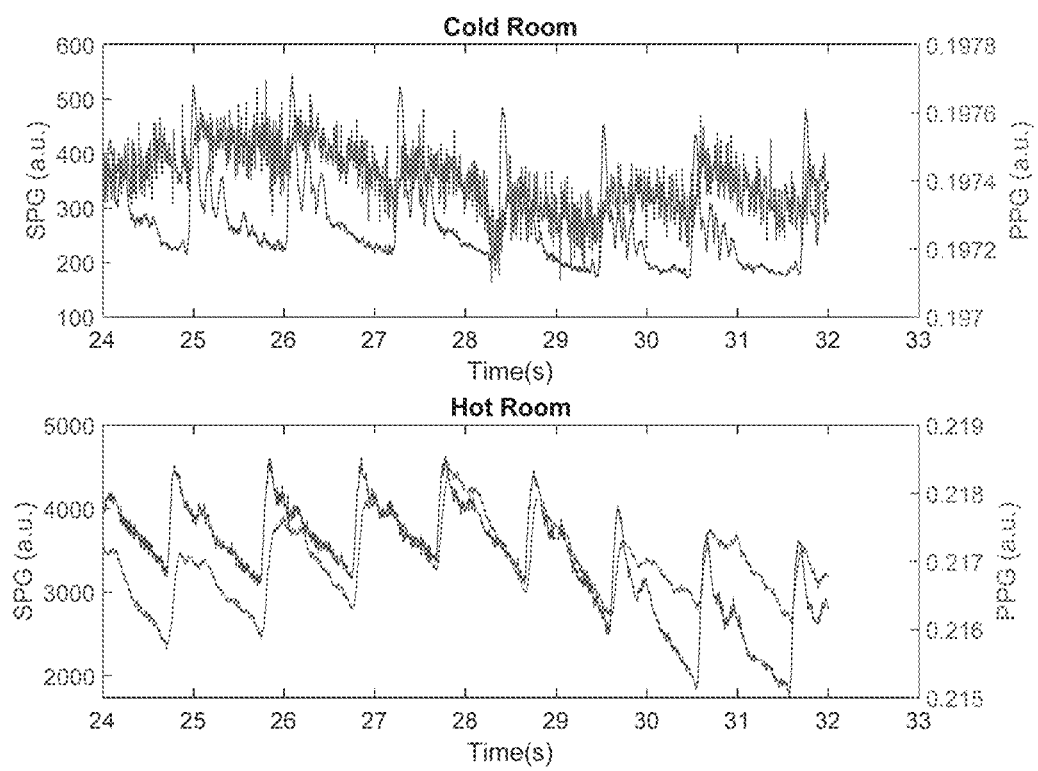
FIG. 6(c) depicts subject 3.
Figure 7A:
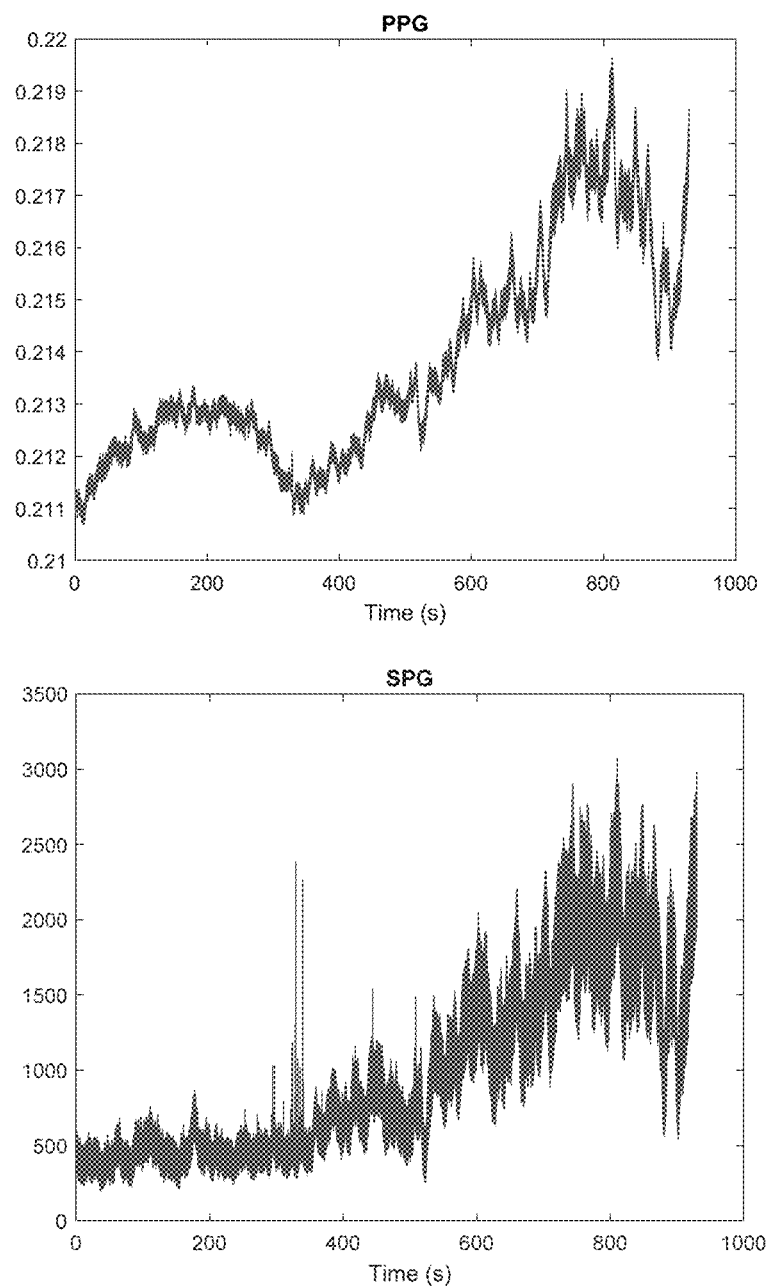
FIG. 7(a) depicts results of Subject 1.
Figure 7A:
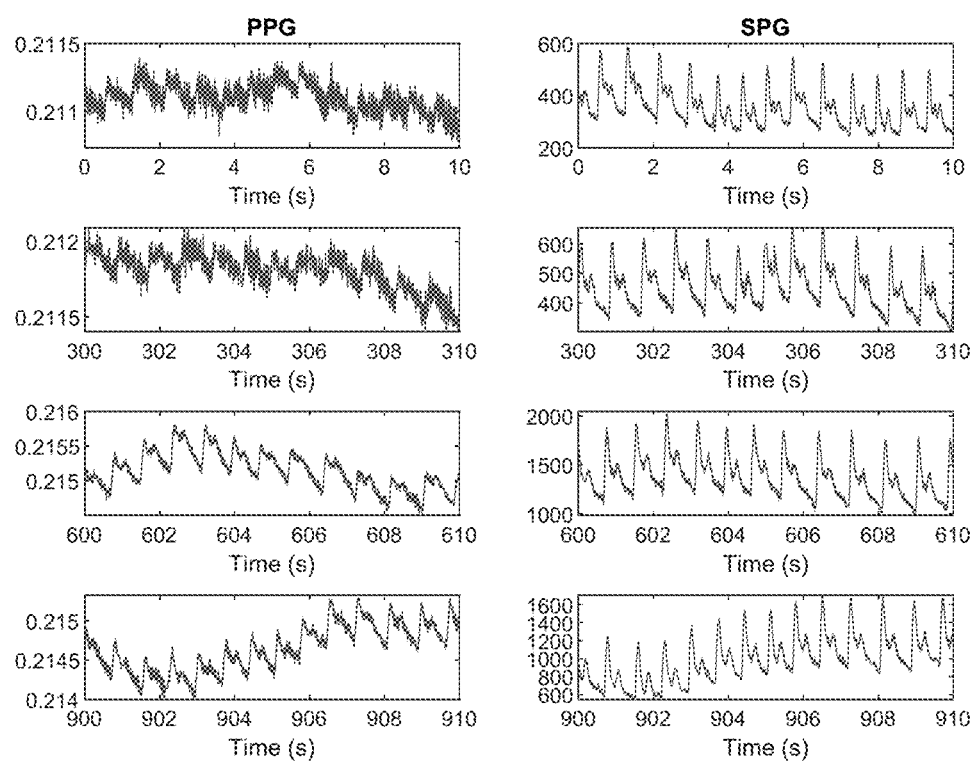
Figure 7B:
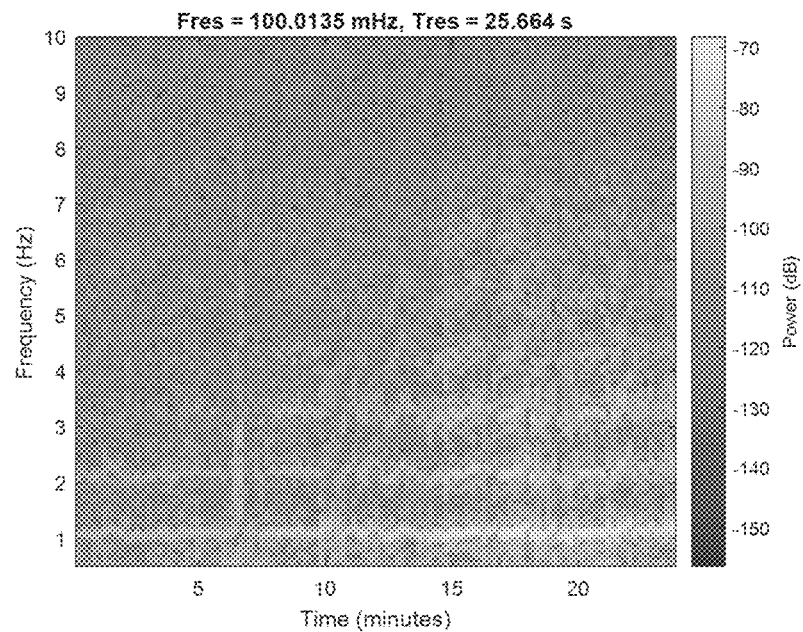
FIG. 7(b) depicts results of Subject 2.
Figure 7B:
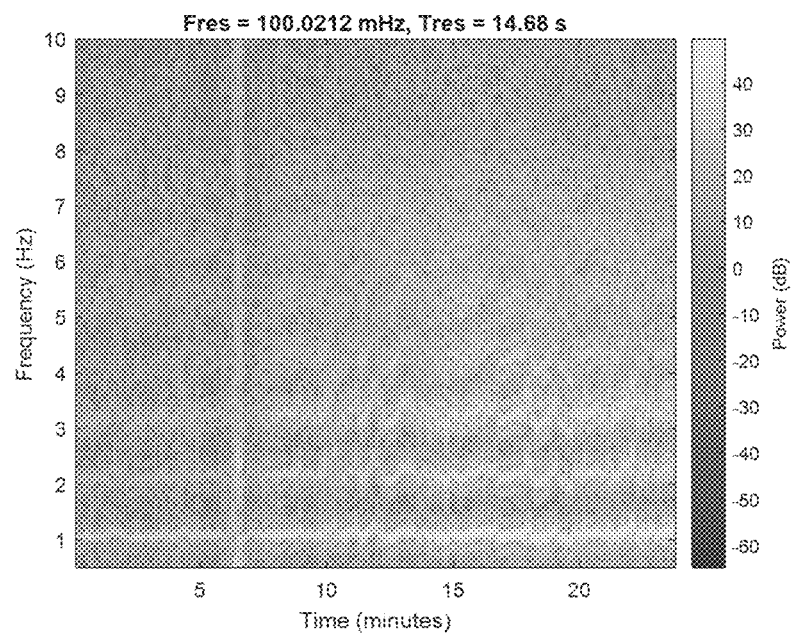
Figure 7B:
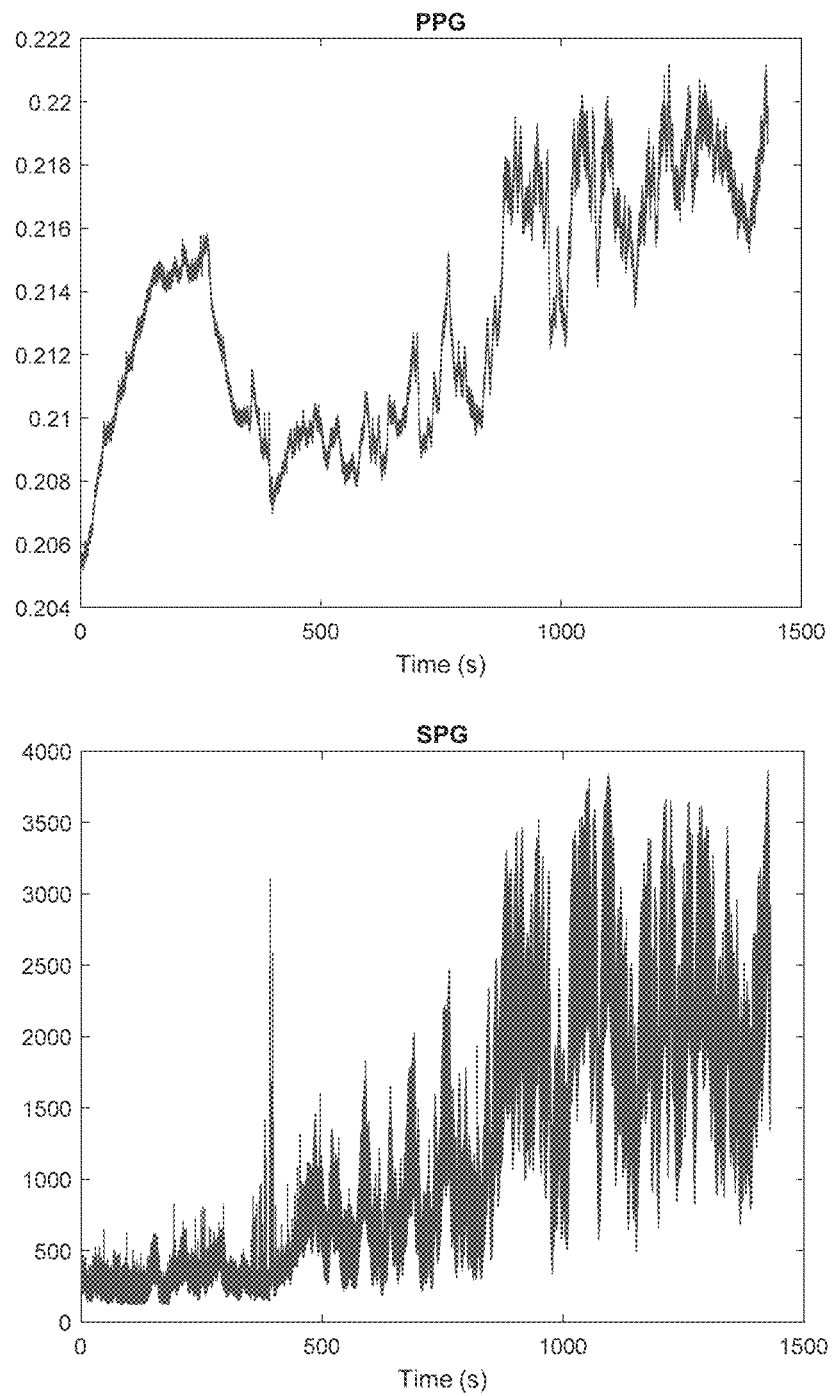
Figure 7B:
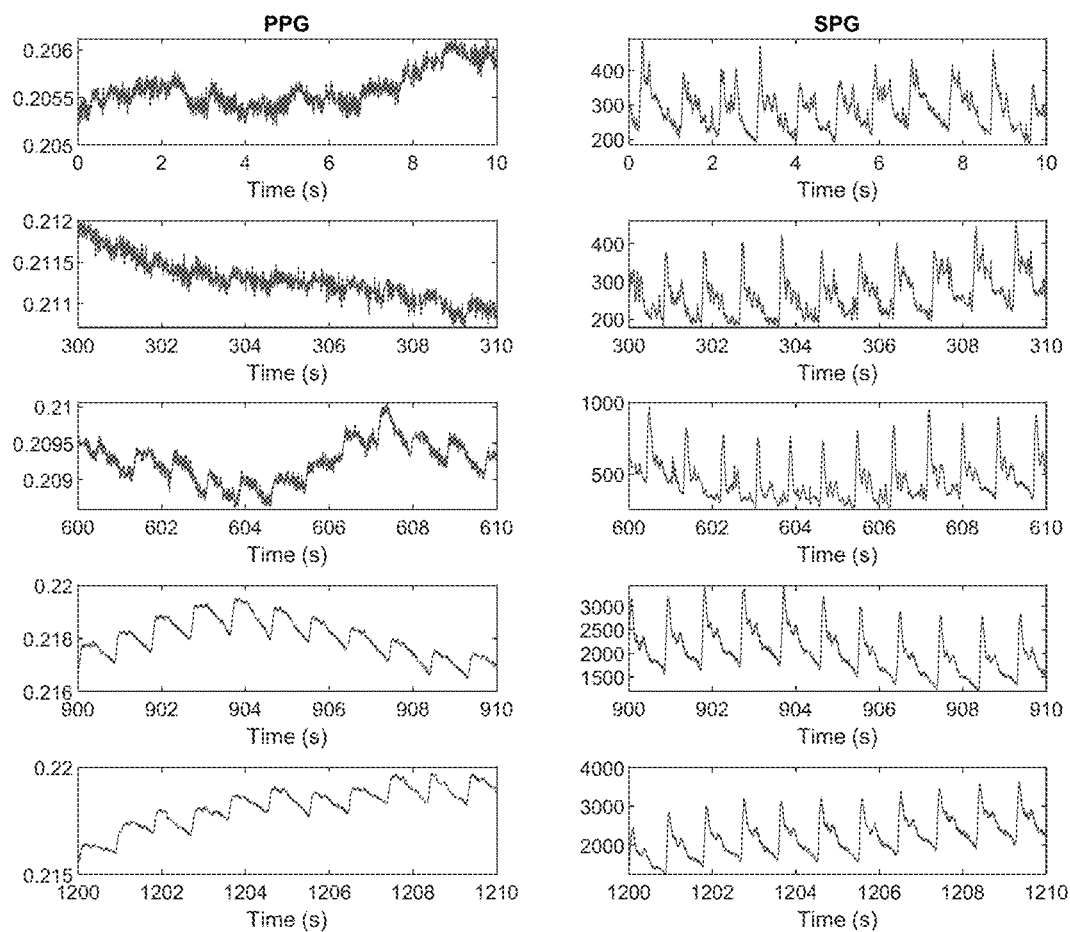
Figure 7C:
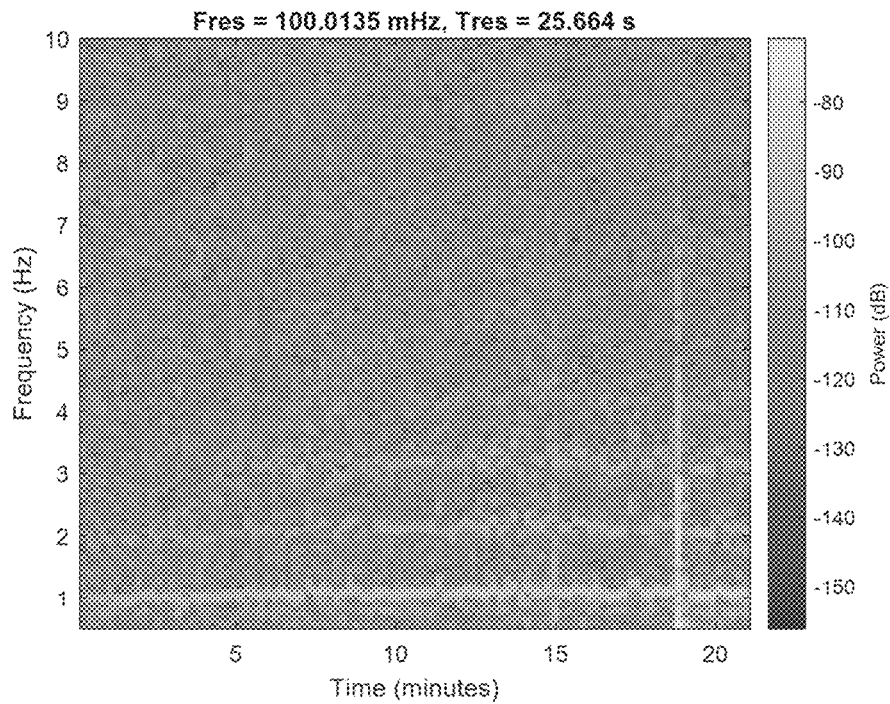
FIG. 7(c) depicts results of Subject 3.
Figure 7C:
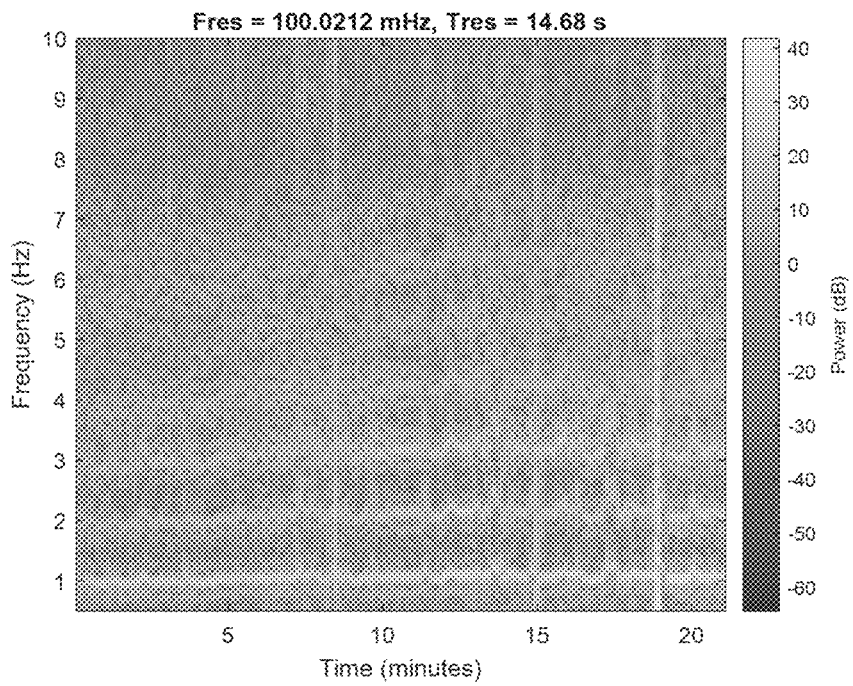
Figure 7C:
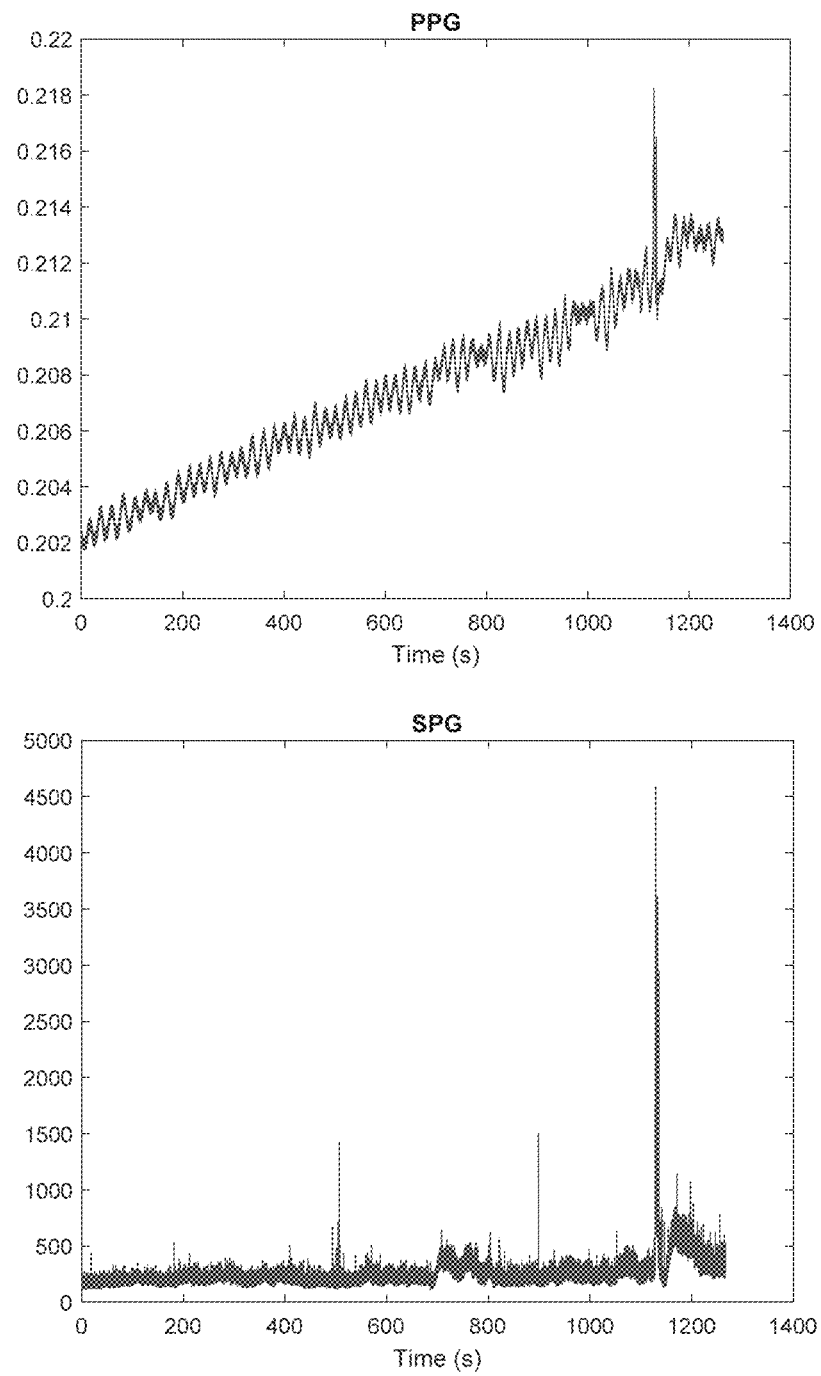
Figure 7C:
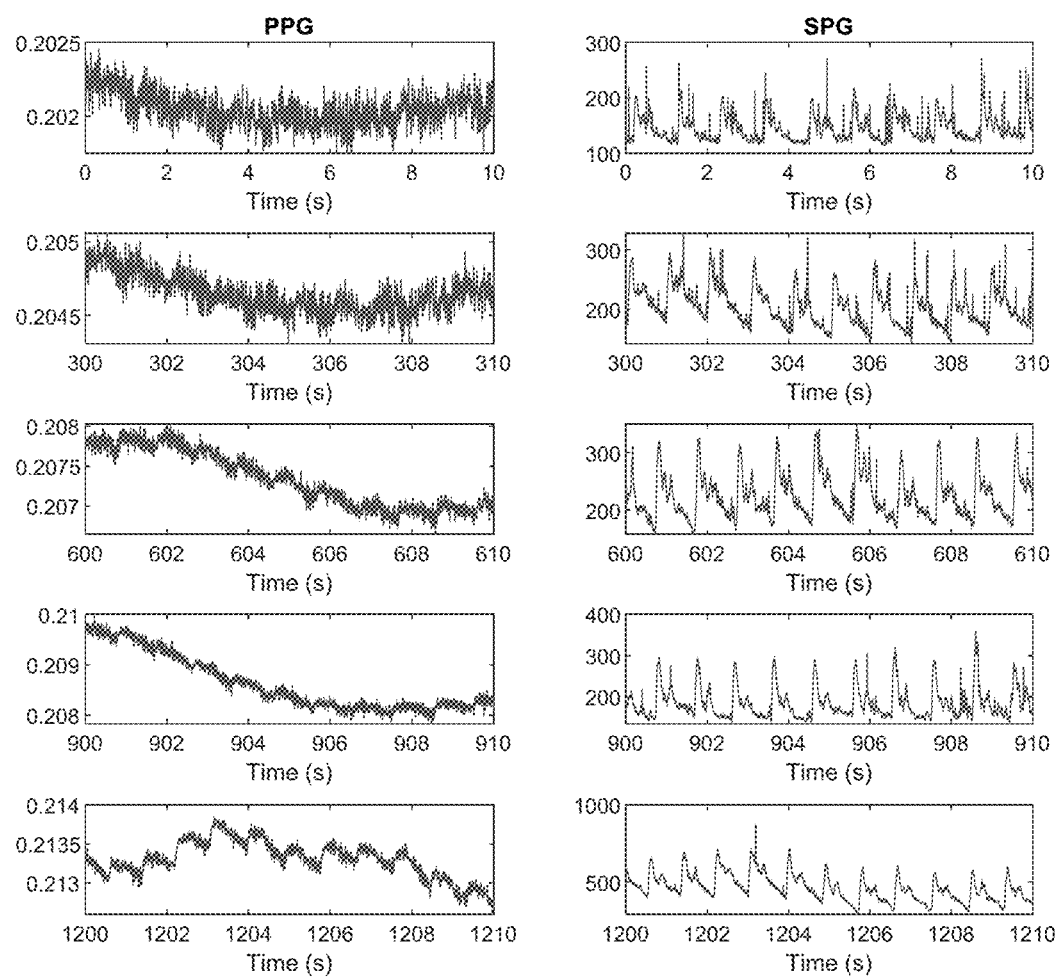
Figure 8:
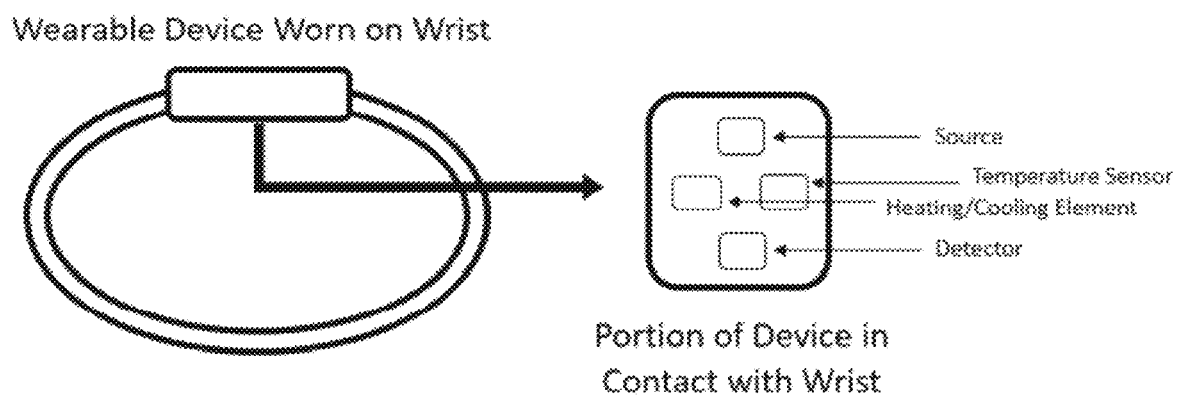
FIG. 8 depicts, in accordance with various embodiments herein, an example of a model of health and vascular monitoring device that is to be worn around the wrist of the user.

All references, publications, and patents cited herein are incorporated by reference in their entirety as though they are fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, N.Y. 2001); March, Advanced Organic Chemistry Reactions, Mechanisms and Structure 7th ed., J. Wiley & Sons (New York, N.Y. 2013); and Sambrook and Russel, Molecular Cloning: A Laboratory Manual 4th ed., Cold Spring Harbor Laboratory Press (Cold Spring Harbor, N.Y. 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As used herein, the term "PPG" refers to photoplethysmography.

As used herein, the term "SPG" refers to speckleplethysmogram.

As described herein, the inventors have developed a peripheral device for testing and monitoring vascular health metrics such as endothelial function, arterial stiffness, and blood pressure. In one embodiment, the present invention provides a small heating/cooling component placed on a human digit to alter local blood flow dynamics. In another embodiment, vascular health is monitored by using a coherent source and detector to compare laser speckle contrast and photoplethysmography (PPG) signals acquired from the same digit.

Reviewing FIG. 1 herein in more detail, devices for monitoring and assessing health, and components thereof are illustrated. In one embodiment, the present invention provides a device for monitoring and assessing health, comprising a heating/cooling component 101, coherent source 102, temperature sensor 103, image detector 104, and/or wiring 105. In another embodiment, the wiring is to a power source and control circuitry and image processing. In another embodiment, data analysis and control may be performed wirelessly. In another embodiment, the device is a rigid encasing model as depicted. In another embodiment, the device is a model of relative flexible circuitry and design as depicted.

In another embodiment, the invention provides a device comprising a heating component, a temperature sensor, a coherent source, and a detector, wherein the device is in a small package to noninvasively monitor local changes in vascular health without a cuff or pressure sensor. In another embodiment, a comparison of the changes in the speckleplethysmogram (SPG) and PPG allow for characterization of the vasculature, endothelial function, and perfusion.

In one embodiment, the present invention provides a device that monitors a subject's health and wellness by providing accurate, noninvasive measurements of their peripheral vasculature, including measuring fitness levels as well as overall cardiovascular health.

In one embodiment, the present invention provides a device for managing and/or monitoring vascular health, comprising an apparatus that attaches to a subject's finger comprising a heating and cooling component, a coherent source, a temperature sensor, an image detector, and/or a component for data control and management. In another embodiment, the component for data control and management comprises wiring to a power source, control circuitry, and/or image processing. In another embodiment, the component for data control and management is wireless. In another embodiment, the apparatus is a clip to the finger. In another embodiment, the apparatus is a flexible design.

In another embodiment, the present invention provides a method of managing and/or monitoring vascular health in an individual, comprising providing a device comprising an apparatus that attaches to a subject's finger comprising a heating and cooling component, a coherent source, a temperature sensor, an image detector, and/or a component for data control and management, and using the device to manage and/or monitor vascular health in the individual. In another embodiment, the apparatus is clipped to the finger of the individual.

In another embodiment, the present invention provides a device for monitoring vascular health in a subject, comprising a heating/cooling component that alters local blood flow in the subject, and an apparatus that compares laser speckle contrast and photoplethysmography (PPG) signals from the altered blood flow in the subject. In another embodiment, the vascular health is monitored using a coherent source and a detector that compares the laser speckle contrast and PPG.

In another embodiment, the heating/cooling component is attached as a clip to the subject's finger.

In another embodiment, the present invention provides a method of diagnosing susceptibility to a disease and/or condition in a subject, comprising providing a device for monitoring vascular health in a subject, comprising a heating/cooling component that alters local blood flow in the subject and an apparatus that compares laser speckle contrast and photoplethysmography (PPG) signals from the altered blood flow in the subject, and diagnosing susceptibility to the disease based on the presence of one or more biomarkers.

In another embodiment, the present invention provides a method of treating a disease and/or condition in a subject, comprising providing a device for monitoring vascular health in a subject, comprising a heating/cooling component that alters local blood flow in the subject and an apparatus that compares laser speckle contrast and photoplethysmography (PPG) signals from the altered blood flow in the subject, and treating the subject. In another embodiment, the disease and/or condition is related to vascular health. In another embodiment, the device is part of an overall treatment regimen.

As readily apparent to one of skill in the art, various embodiments herein may be used in conjunction with multiple wavelengths, multiple exposure times, and/or multiple detectors. For example, in one embodiment, wavelengths may range from visible to near infrared. Or, for example, multiple wavelengths could aid in the calculation of oxygen saturation. In another embodiment, for example, multiple exposure times could range from 0.05 ms to 80 ms. In another embodiment, multiple exposure times could range from 0.02 ms to 100 ms. For example, in one embodiment, using more than one exposure time could aid in establishing baseline flow measurements that are quantitative. In another embodiment, the present invention provides multiple detectors. For example, in one embodiment, the present invention provides a first detector to measure SPG, and a second detector to measure PPG. In another embodiment, the SPG detector is a camera sensor. In another embodiment, the PPG detector could be a photodiode.

Similarly, as readily apparent to one of skill the art, in conjunction with various embodiments further described herein, the invention is in no way limited to only use on a individual's finger. For example, in one embodiment, the device also could be used on a toe. Or, for example, in one embodiment, the device could be used on an individual's entire hand or foot, such as for example, to be used on a neonates/premature infant.

EXAMPLES

Example 1

Generally

The inventors have developed a peripheral device for testing and monitoring vascular health metrics such as endothelial function, arterial stiffness, and blood pressure. In one embodiment, the present invention provides a small heating/cooling component placed on a human digit to alter local blood flow dynamics. In another embodiment, vascular health is monitored by using a coherent source and detector to compare laser speckle contrast and photoplethysmography (PPG) signals acquired from the same digit.

The device is novel in that it combines a heating component with a temperature sensor, coherent source, and detector in a small package to noninvasively monitor local changes in vascular health without a cuff or pressure sensor. A comparison of the changes in the speckleplethysmogram (SPG) and PPG allow for characterization of the vasculature, endothelial function, and perfusion. The inventors have also collected supportive data, demonstrating that heat improves signal quality for SPG and PPG and modeled a small heating component on a finger to demonstrate sufficient changes in temperature. The temperature changes are important because they cause vasodilation and vasoconstriction of the vasculature, which in turn provides the necessary information-rich dynamics.

Example 2

Some Advantages

Some advantages include that the device is noninvasive, utilizes small, inexpensive components, and does not require an uncomfortable cuff for an occlusion. Furthermore, the heating dynamics are relatively quick, reducing measurement time. SPG/PPG measurements without temperature regulation do not have the controlled conditions or signal quality required for dynamic measurements while at rest.

Furthermore, while other commercially available devices have integrated heart rate variability technology, but they have limited accuracy and reliability. Also, alternative commercially available devices such as monitoring endothelial function requires expensive equipment, and generally only available to healthcare professionals. In contrast, the inventors have developed a device that uses a novel source and detector to take advantage of a stronger physiological signal based on blood flow, which allows for more accurate estimations of heart rate variability. Furthermore, in accordance with various embodiments herein, the device may thermally control dilation of blood vessels to approximate endothelial function by monitoring the rate of vessel expansion. Thus, the inventors have developed a device that enables accurate and repeatable measurements for longitudinal tracking of dietary and fitness goals.

Example 3

A Need in the Art

Individuals with a range of health and activity levels have incorporated fitness devices into their daily practices, describing a strong attachment to them and, importantly, citing them as motivation for improving their health practices. Despite the strides made in the fitness device landscape, users are often unsatisfied with the accuracy and relevance of their devices. Accuracy is an important factor for consumers when deciding to buy a fitness device. The availability of online information has made today's users more educated and, thus, they demand higher quality information that will help them realize their fitness and healthcare goals. Aging populations, such as the ones found in the U.S., are frustrated with diet and fitness trends that do not provide the promised results. In accordance with various embodiments herein, the inventors aim to address a critical, unmet need of helping individuals aged 55 and over increase not only their quantity of life, but their quality of life by providing simple, accurate metrics directly related to the health of their cardiovascular physiology.

Example 4

An Example of a Vascular Health Device

In one embodiment, the invention provides a finger-clip device that plugs into a smartphone charging port. Users may download the corresponding application and then take five minute measurements while at rest. During the measurement, a light may shine through the finger and is collected by a sensor, while the clip casing systematically controls the temperature of the finger. The device may estimate heart rate variability and endothelial function by calculating changes in blood flow due to expanding and contracting blood vessels. Heart rate variability, the deviation between heart beats, is otherwise commonly used to look at fitness and stress levels. Endothelial function, the ability of blood vessels to expand and contract, is an important metric for monitoring cardiovascular health as it correlates highly to risk of heart attack and stroke. Importantly, both heart rate variability and endothelial function can be improved with exercise and proper diet, making the device the ideal health and wellness tracking device.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps, some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a," "an," and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety. In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A device for managing and/or monitoring vascular health of a subject, comprising
   an apparatus that is configured to be attached to a digit of the subject, the apparatus comprising the following components:
   a heating component that is configured to generate localized heating of a subject's digit;
   a cooling component that is configured to generate localized cooling of a subject's digit;
   a temperature sensor that is configured to measure or monitor the temperature of the subject's digit;
   a coherent light source that is configured to emit light onto the digit of the subject;
   an image detector that is configured to acquire images of the subject's digit interacting with the coherent light source;
   a casing or housing that comprises the components of the apparatus and which is dimensioned or designed to accommodate or be applied to the digit of the subject,
   wherein the heating component and cooling component are separate components or alternatively, are combined into a single heating/cooling component, and wherein the localized heating generated by the heating component and/or localized cooling generated by the cooling component alter the local blood flow dynamics in the digit of the subject, and wherein the image detector is used to record or monitor the blood flow dynamics of the digit of the subject.

2. The device of claim 1, wherein device further comprises a component for data control and management, and wherein the component for data control and management processes and/or analyzes images acquired by the one or more image detector(s).

3. The device of claim 1, wherein the device further comprises a component for data control and management, and wherein the component for data control and management is connected to the apparatus by a physical connection or by a wireless connection.

4. The device of claim 1, wherein the casing or housing is configured to either clip onto the digit or slidably accommodate the digit.

5. The device of claim 1, wherein the casing or housing is configured to flexibly wrap around the digit.

6. The device of claim 1, wherein the detector utilizes multiple exposure times to acquire images of the digit, and wherein the images of the digit are laser speckle contrast images.

7. The device of claim 6, wherein the multiple exposure times that range from 0.02 ms to 100 ms.

8. The device of claim 1, wherein the coherent light source emits light having a wavelength that ranges from visible to near infrared.

9. The device of claim 1, wherein the apparatus further comprises additional light source(s) and detector(s), and wherein multiple wavelengths of light are emitted onto the digit of subject using the additional light source(s), and wherein the detector(s) are used to measure the reflected light from the digit in order to determine the subject's oxygen saturation.

10. The device of claim 1, wherein the image detector uses more than one exposure time to establish quantitative baseline flow measurements.

11. The device of claim 1, wherein the image detector is used to obtain speckleplethysmography signals, and wherein the apparatus comprises additional light source(s) and detector(s) to obtain a photoplethysmography signals.

12. The device of claim 11, wherein the image detector used to obtain the speckleplethysmography signals is selected from a camera sensor, a photodetector, and/or an array of photodiodes.

13. The device of claim 11, wherein the detector(s) used to obtain the photoplethysmography signals is selected from a camera sensor, a photodetector and/or a photodiode.

14. A device for monitoring vascular health in a subject, comprising:
   a heating/cooling component that alters local blood flow in the subject; and
   an altered blood flow imaging component that comprises a coherent light source and an image detector to acquire speckleplethysmography signals, and additional light source(s) and detector(s) to measure photoplethysmography signals from the altered local blood flow in the subject;
   wherein the speckleplethysmography signals and the photoplethysmography signals are used to monitor the subject's vascular health.

15. The device of claim 14, wherein the speckleplethysmography signals and photoplethysmography signals are indicative of the subject's endothelial function.

16. The device of claim 14, wherein the heating/cooling component is attached as a clip to a digit of the subject.

17. The device of claim 14, wherein the device is worn around the wrist of the subject.

18. A method of diagnosing susceptibility to a disease and/or condition in a subject, comprising;
   using the device of claim 11 on a digit of the subject to measure local blood flow dynamics by altering the blood flow in the subject's digit using the heating and/or cooling component and generating speckleplethysmography signals and photoplethysmography signals from the altered blood flow in the subject's digit; and
   analyzing the speckleplethysmography signals and photoplethysmography signals from the subject for arterial stiffness and/or endothelial function;
   wherein the subject is susceptible to a disease and/or condition if the speckleplethysmography signals and photoplethysmography signals indicate reduced endothelial function and/or arterial stiffness.

19. The method of claim 18, wherein the disease is related to cardiovascular health.

20. The method of claim 18, wherein the subject is a neonate and/or premature infant.

* * * * *